(12) United States Patent
Wales et al.

(10) Patent No.: US 8,535,338 B2
(45) Date of Patent: Sep. 17, 2013

(54) SYSTEM AND METHOD FOR INTERVERTEBRAL DISC BULGE REDUCTION

(75) Inventors: Lawrence W. Wales, Maplewood, MN (US); Jean-Pierre Mobasser, Indianapolis, IN (US); Thomas A. Zdeblick, Minnetonka, MN (US); John E. Sherman, Minnetonka, MN (US)

(73) Assignee: Anulex Technologies, Inc., Minnetonka, MN (US)

( * ) Notice: Subject to any disclaimer, the term of this patent is extended or adjusted under 35 U.S.C. 154(b) by 159 days.

(21) Appl. No.: 13/037,820

(22) Filed: Mar. 1, 2011

(65) Prior Publication Data

US 2011/0295276 A1    Dec. 1, 2011

Related U.S. Application Data

(60) Provisional application No. 61/339,206, filed on Mar. 1, 2010.

(51) Int. Cl.
*A61B 17/00*    (2006.01)
*A61B 17/10*    (2006.01)

(52) U.S. Cl.
USPC ............. 606/139; 623/17.11; 623/17.16

(58) Field of Classification Search
USPC ................ 606/139; 623/17.11–17.16
See application file for complete search history.

(56) References Cited

U.S. PATENT DOCUMENTS

| | | | |
|---|---|---|---|
| 6,245,107 B1 * | 6/2001 | Ferree | 606/279 |
| 2004/0260397 A1 | 12/2004 | Lambrecht et al. | |
| 2006/0121084 A1 | 6/2006 | Borden et al. | |
| 2006/0271198 A1 * | 11/2006 | McAfee | 623/17.16 |
| 2007/0100348 A1 | 5/2007 | Cauthen, III et al. | |
| 2007/0288040 A1 | 12/2007 | Ferree | |
| 2010/0016889 A1 | 1/2010 | Ferree | |

OTHER PUBLICATIONS

International Search Report and Written Opinion issued in PCT/US2011/026644, mailed May 23, 2011, 15 pages.

* cited by examiner

*Primary Examiner* — Kevin T Truong
*Assistant Examiner* — Christian Sevilla
(74) *Attorney, Agent, or Firm* — Faegre Baker Daniels LLP

(57) ABSTRACT

A system and method for treating a bulge in an intervertebral disc annulus fibrosus adjacent to a vertebral body of a patient's spine using a repair device including a suture element, a patch element and a bone anchor. A bore is formed through a portion of the vertebral body, including an endplate thereof adjacent to the intervertebral disc. A suture picker is deployed through the bore and the annulus fibrosus, and the suture element is coupled to the suture picker. The suture picker is withdrawn from the bore. The suture element is pulled so as to draw the patch element against the bulge, and continued tension on the suture element urges the patch and the bulged anteriorly so as to re-approximate the natural shape of the annulus fibrosus. The suture element is secured to the vertebral body using the bone anchor.

22 Claims, 5 Drawing Sheets

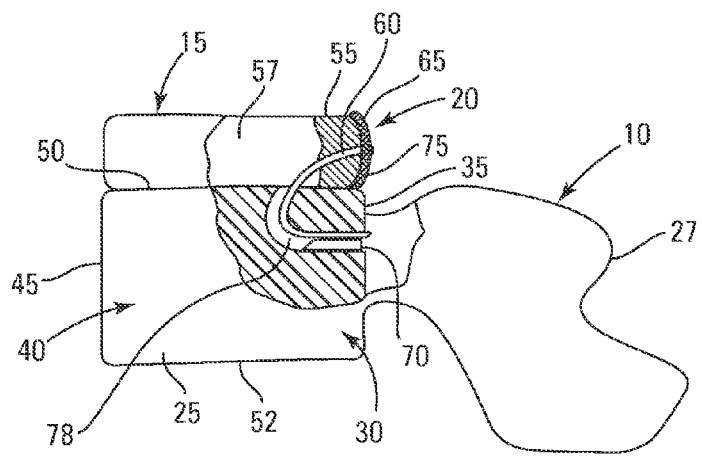
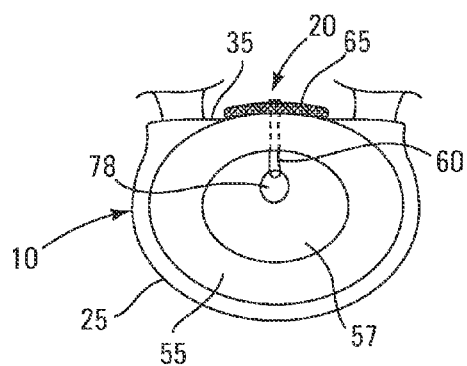 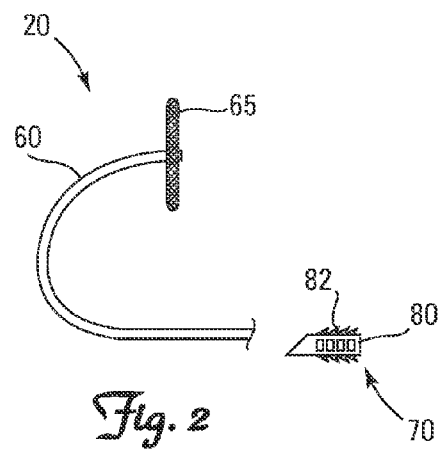

SYSTEM AND METHOD FOR INTERVERTEBRAL DISC BULGE REDUCTION

CROSS-REFERENCE TO RELATED APPLICATION

This application claims the benefit of U.S. Provisional Application No. 61/339,206, filed Mar. 1, 2010, entitled "System and Method for Intervertebral Disc Bulge Reduction," which is incorporated herein by reference in its entirety.

TECHNICAL FIELD

The present invention relates to devices and methods for orthopedic repair. More specifically, the invention relates to devices and methods for repairing the intervertebral disc of the spine.

BACKGROUND

The spinal column is formed from a number of bony vertebrae, which in their normal state are separated from each other by intervertebral discs. These discs are comprised of the annulus fibrosus, and the nucleus pulposus, both of which are soft tissue. The intervertebral disc acts in the spine as a crucial stabilizer, and as a mechanism for force distribution between adjacent vertebral bodies. Without a competent disc, collapse of the intervertebral disc may occur, contributing to abnormal joint mechanics and premature development of degenerative and/or arthritic changes.

The normal intervertebral disc has an outer ligamentous ring called the annulus surrounding the nucleus pulposus. The annulus binds the adjacent vertebrae together and is constituted of collagen fibers that are attached to the vertebrae and cross each other so that half of the individual fibers will tighten as the vertebrae are rotated in either direction, thus resisting twisting or torsional motion. The nucleus pulposus is constituted of soft tissue, having about 85% water content, which moves about during bending from front to back and from side to side.

The aging process contributes to gradual changes in the intervertebral discs. Fissures in the annulus fibrosus can occur due to various causes, including disease or other pathological conditions, or the natural aging process. Occasionally fissures may form rents through the annular wall. In these instances, the nucleus pulposus is urged outwardly from the subannular space through a rent, often into the spinal column. Extruded nucleus pulposus can, and often does, mechanically press on the spinal cord or spinal nerve rootlet. This painful condition is clinically referred to as a ruptured or herniated disc.

In the event of annulus rupture, the subannular nucleus pulposus migrates along the path of least resistance forcing the fissure to open further, allowing migration of the nucleus pulposus through the wall of the disc, with resultant nerve compression and leakage of chemicals of inflammation into the space around the adjacent nerve roots supplying the extremities, bladder, bowel and genitalia. The usual effect of nerve compression and inflammation is intolerable back or neck pain, radiating into the extremities, with accompanying numbness, weakness, and in late stages, paralysis and muscle atrophy, and/or bladder and bowel incontinence. Additionally, injury, disease or other degenerative disorders may cause one or more of the intervertebral discs to shrink, collapse, deteriorate or become displaced, herniated, or otherwise damaged and compromised.

SUMMARY

In Example 1, the present invention is a method of reducing a bulge in an intervertebral disc annulus fibrosus adjacent to a vertebral body of a patient's spine, the vertebral body having a posterior surface and an end plate adjacent to the annulus fibrosus. The method comprises first forming a bore through a portion of the vertebral body, the bore extending from the posterior surface and through end plate, and advancing a suture picker through the bore and into the intervertebral disc. Next, a distal end of the suture picker is advanced through an outer surface of the annulus fibrosus at a location within or proximate the bulge. The distal end of the suture picker is engaged with a portion of a flexible suture element connected to a flexible patch element. The distal end of the suture picker and the portion the suture element engaged therewith are then retracted proximally through the annulus fibrosus and the bore in the vertebral body, such that the portion of the suture element is positioned external to the vertebral body. Tension is applied to the portion of the suture element so as to draw the patch element against the outer surface of annulus fibrosus at the location within or proximate the bulge and urge the annulus fibrosus within or proximate the bulge toward an anterior portion of the annulus fibrosus. The suture element is then secured under tension.

In Example 2, the method of Example 1 wherein applying tension to the portion of the suture element substantially reshapes the annulus fibrosus to substantially its natural shape.

In Example 3, the method of either of Examples 1 or 2 wherein forming the bore includes forming a first bore segment with a first boring tool, and subsequently forming a second bore segment distal to the first bore segment using a second boring tool.

In Example 4, the method of Example 3 wherein the first bore segment extends generally parallel to the end plate, and wherein the second bore segment extends distally from the first bore segment along a curved path toward and through the end plate.

In Example 5, the method of either of Examples 3 or 4 wherein the first boring tool is a bone awl having a generally straight working shaft, and wherein the second boring tool includes a flexible distal end portion pre-shaped so as to define the curved path.

In Example 6, the method of any of Examples 3-5 wherein forming the bore further includes inserting a generally rigid tubular cannula into the first bore segment prior to forming the second bore segment.

In Example 7, the method of any of Examples 3-6 wherein forming the second bore segment includes advancing the second boring tool through the tubular cannula, the tubular cannula maintaining the flexible distal end portion of the second boring tool in a deflected, substantially straight configuration.

In Example 8, the method of any of Examples 5-7 wherein the flexible distal end portion of the second boring tool is configured to assume its pre-shaped configuration once extended beyond the tubular cannula so as to form the second bore segment upon advancement through the vertebral body distal to the tubular cannula.

In Example 9, the method of any of Examples 1-8 wherein the suture picker includes a proximal portion and a flexible, pre-shaped distal portion including the distal end, the pre-shaped distal portion configured to direct the distal end toward the annulus fibrosus when the proximal portion is at least partially disposed within the bore.

In Example 10, the method of any of Examples 1-9 wherein the distal end includes an engagement feature for engaging the suture element.

In Example 11, the method of any of Examples 1-10 wherein the suture element includes a suture loop for engaging the engagement feature of the suture picker.

In Example 12, the method of any of Examples 1-11 wherein advancing the distal end of the suture picker through the outer surface of the annulus fibrosus includes advancing the distal end through an opening in the annulus fibrosus within the bulge.

In Example 13, the method of Example 12 wherein the opening is an incision made by a clinician during a discectomy procedure.

In Example 14, the method of any of Examples 1-13 wherein securing the suture element under tension includes securing the suture element to the vertebral body.

In Example 15, the method of Example 14 wherein securing the suture element to the vertebral body includes deploying a bone anchor into the bore and securing the bone anchor to the suture element and to the vertebral body within the bore with the suture element maintained in tension.

In Example 16, the method of Example 15 wherein the bone anchor includes a channel, and wherein attaching the bone anchor to the suture element includes positioning an end of the suture element within the channel and advancing the bone anchor along the suture element.

In Example 17, the method of Example 16 wherein advancing the bone anchor along the suture element includes advancing the bone anchor along the suture element and into the bore in the vertebral body, and wherein attaching the bone anchor to the vertebral body includes attaching the bone anchor to the vertebral body within the bore.

In Example 18, the method of any of Examples 15-17 wherein securing the suture element to the vertebral body includes securing a portion of the suture element between the bone anchor and the inner surface of the bore.

In Example 19, the method of Example 18 wherein securing the bone anchor to the vertebral body within the bore includes forming an interference fit between the bone anchor and an inner surface of the bore.

In Example 20, the method of any of Examples 15-19 wherein the bone anchor includes a bone engagement feature, and wherein attaching the bone anchor to the vertebral body includes engaging the vertebral body with the bone engagement feature.

In Example 21, the method of Example 20 wherein the bone engagement feature includes one or more barbs or projections configured to allow the bone anchor to be advanced distally within the bore and to inhibit subsequent proximal movement of the bone anchor within the bore toward the posterior surface of the vertebral body.

In Example 22, the method of any of Examples 15-21 wherein attaching the bone anchor to the suture element includes deploying a locking element prevent relative movement of the bone anchor and the suture element after attaching the bone anchor to the vertebral body.

In Example 23, the method of Example 22 wherein the locking element is a knot or a pledget.

In Example 24, a system for treating a defect in an annulus fibrosus of an intervertebral disc of a patient, the system comprising a repair device, a bone boring tool, and a flexible suture picker. The repair device includes a flexible suture element, a flexible patch element coupled thereto, and a bone anchor configured to be coupled to the suture element and to a vertebral body adjacent to the intervertebral disc. The bone boring tool has a proximal portion and a flexible distal end portion, the flexible distal end portion having a pre-shaped curvature and a distal tip configured to penetrate bone. The flexible suture picker includes a proximal portion and a pre-shaped distal portion including a distal end, the distal end including an engagement feature for releasably engaging the suture element during deployment of the repair device.

In Example 25, the system of Example 24 wherein the bone anchor includes a body, a channel extending longitudinally therethrough sized to slidably receive a length of the suture element, and a bone engagement feature on the body configured to allow the bone anchor to be advanced distally within a bore in a vertebral body adjacent to the annulus fibrosus and to inhibit subsequent proximal movement of the bone anchor within the bore.

In Example 26, the system of either of Examples 24 or 25 wherein the bone engagement feature includes one or more barbs or projections extending radially from the body.

In Example 27, the system of any of Examples 24-26 wherein the repair device further includes a locking feature configured to lock the bone anchor in place with respect to the suture element.

In Example 28, the system of Example 24 wherein the bone anchor is sized to form an interference fit within a bore in the vertebral body so as to secure the suture element and the bone anchor to the vertebral body when implanted.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 1A-1B are partial cut-away elevation and plan views of a vertebra and an adjacent intervertebral disc after treatment of the disc using an implantable repair device according to one embodiment of the present invention.

FIG. 2 is an illustration of the repair device of FIGS. 1A and 1B.

Figure 3A:
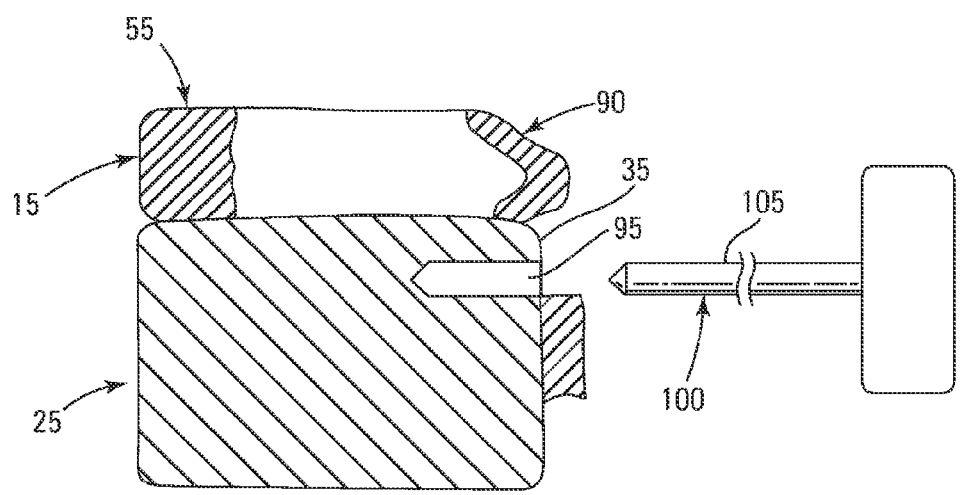
FIGS. 3A-3G are partial cross-sectional elevation views illustrating repairing an annulus fibrosus of an intervertebral disc using the repair device of FIGS. 1A-1B and 2.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIGS. 1A-1B are partial cut-away elevation and plan views of a vertebra 10 and an adjacent intervertebral disc 15 after treatment of the disc 15 using an implantable repair device 20, and FIG. 2 is a schematic illustration of the repair device 20, according to one embodiment of the present invention. As shown in FIGS. 1A-1B, the vertebra body 10 includes a main vertebral body 25 and a spinous process 27. As further shown, the vertebra 25 includes a posterior region 30 having a posterior surface 35, an anterior region 40 having an anterior surface 45, and opposed superior and inferior end plates 50, 52. As illustrated, the intervertebral disc 15 bears against the superior end plate 50 and includes an outer annulus fibrosus 55 surrounding an interior nucleus pulposus 57.

As further shown, the repair device 20 includes a flexible suture element 60, a flexible patch element 65, and a bone anchor 70. The suture element 60 is coupled to the patch element 65, and the bone anchor 70 is configured to couple to the suture element 60 and to the vertebral body 25 adjacent to anchor the repair device 20 thereto.

As will be explained in further detail herein, the repair device 20 is configured to be deployed to treat (i.e., reduce) a bulge in the annulus fibrosus 55 such as can be present in a diseased disc 15. As explained earlier, such bulges in the annulus fibrosus 55 can tend to impinge on nerves proximate to the bulged region. The repair device 20 is configured to substantially reshape the annulus fibrosus 55 to its natural shape and thereby substantially eliminate the aforementioned bulge therein and the associated medical consequences. Thus, as shown in FIGS. 1A and 1B, the patch element 65 bears against an external surface 75 of the annulus fibrosus 55, and the suture element 60 extends from the patch element 65, through the annulus fibrosus 55 and into a bore 78 formed in the vertebral body 25 and extending through the superior end plate 50 and the posterior surface 35 of the vertebral body 25. As further shown, the bone anchor 70 is positioned within the bore 78 and operates to secure the suture element 60 to the vertebral body 25 by engaging the inner surface of the bore 78. In the various embodiments, the suture element 60 is secured to the vertebral body 25 under tension so as to maintain the patch element 65 bearing upon and urging the annulus fibrosus 55 anteriorly to substantially assume its natural shape.

In various embodiments, the bone anchor 70 includes a body 80 and an engagement feature 82 configured to allow the bone anchor 70 to be inserted into the bore 78 but which engage the inner surface of the bore 78 once inserted and inhibit or prevent spontaneous reverse movement of the bone anchor 70. In one embodiment, the engagement features 82 include one or more radial barbs or projections extending from the body 80. In one embodiment, the bone anchor body 80 is sized to have a diameter greater than the inside diameter of the bore 78 so as to be secured within the bore 78 by an interference fit. In one embodiment, the bone anchor 70 includes a channel (not shown) extending through the body 80 sized to receive the suture element 60, such that the bone anchor 70 can be advanced over or along the suture element 60 during deployment of the bone anchor 70 into the bore 78. In various such embodiments, the repair device 20 may include a locking element (not shown) such as an adjustable knot, a pledget, crimp tube or the like to secure the bone anchor 70 to the suture element 60. In one embodiment, the repair device 20 is configured such that a portion of the suture element 60 is wedged between the bone anchor 70 and the inner surface of the bore 78 to secure the suture element 60 to the vertebral body 25 under tension. Still other configurations of the bone anchor 70 and the means for securing the suture element 60 to the vertebral body 25 under tension may be employed within the scope of the various embodiments of the invention.

The repair device 20 can be made from any of a number of suitable biocompatible materials. For example, the patch element 65 could include a metallic material (e.g., NiTi alloy, Stainless steel, Titanium), or a polymeric material (e.g., polypropylene, polyethylene, polyurethane, polycarbonate urethane, Polyetheretherketone (PEEK), polyester, PET, poly olefin copolymer, polypropylene, polyethylene), or a biodegradable or bioresorbable material (e.g., collagen, cellulose, polysaccharide, polyglycolic acid (PGA), a polylevolactic acid (PPLA), a polydioxanone (PDA) or for example a racemic polylactic acid (PDLLA), or a combination of these materials. Additionally, they bone anchor 70 be made of any suitable material including, but are not limited to, metals, such as stainless steel, nickel, titanium alloy, and titanium; plastics, such as polytetrafluoroethylene (PTFE), polypropylene, polyether etherketone (PEEK™), polyethylene, polyethylene teraphthalate (PET) and polyurethane, acrylic, polycarbonate, engineering plastics; and/or composites. Similarly, the suture element 60 can likewise be made of any suitable suture material. In various embodiments, the suture element 60 is made wholly or partially of size 2-0 or 3-0 force fiber suture material. In short, any suitable materials, whether now known or later developed, can be utilized to construct the various components of the repair device 20, within the scope of the present invention.

FIGS. 3A-3G are partial cross-sectional elevation views of the vertebral body 25 and disc 15 illustrating a method of repairing the annulus fibrosus 55 of the intervertebral disc 15 using the repair device 20, according to one embodiment of the present invention. As shown in FIG. 3A, the annulus fibrosus 55 includes a bulged region 90. In various embodiments, the bulged region 90 can be caused by one or more of the aforementioned defects or injuries to the annulus fibrosus 55. In various embodiments, the bulged region 90 may include an aperture (not shown) through the thickness of the annulus fibrosus 55, which may occur naturally as a result of a disc herniation, or which may be created by the clinician such as during a discectomy procedure. As further shown, a first bore segment 95 is formed in the vertebral body 25 extending inward from the posterior surface 35. In the illustrated embodiment, the first bore segment 95 extends generally parallel to the superior end plate 50, although in other embodiments, the first bore segment may extend at an angle relative to the end plate 50.

Any suitable instrument can be used to form the first bore segment 95. In the illustrated embodiment, the first bore segment 95 is formed using a conventional bone awl 100 having a generally straight working shaft 105 such as is known in the art. In other embodiments, other instruments may be used to form the first bore segment 95.

Figure 3B:
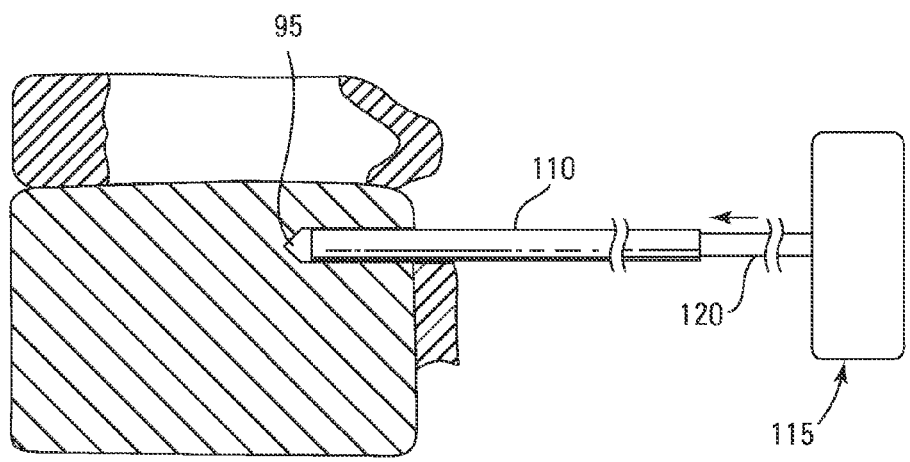
Figure 3C:
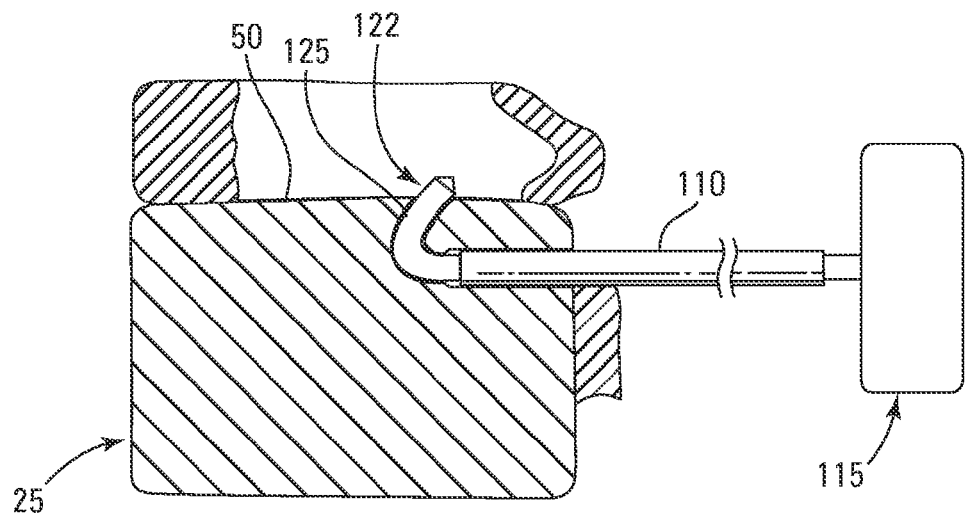

As shown in FIG. 3B, a generally rigid tubular cannula 110 may then be inserted into the first bore segment 95 to provide access to the bore 78 for subsequent aspects of the procedure. As further shown, a second boring tool 115 is inserted into the first bore segment 95 through the cannula 110. As can be seen in FIGS. 3B and 3C, the second boring tool 115 includes a generally straight proximal portion 120 and a flexible distal end portion 122 having a pre-shaped bend 125. The second boring tool 115 is configured to be extendable distally from the cannula 110 so as to allow the clinician to form a second bore segment 130 extending from the first bore segment 95 in a curved path to and through the end plate 50.

Figure 3D:
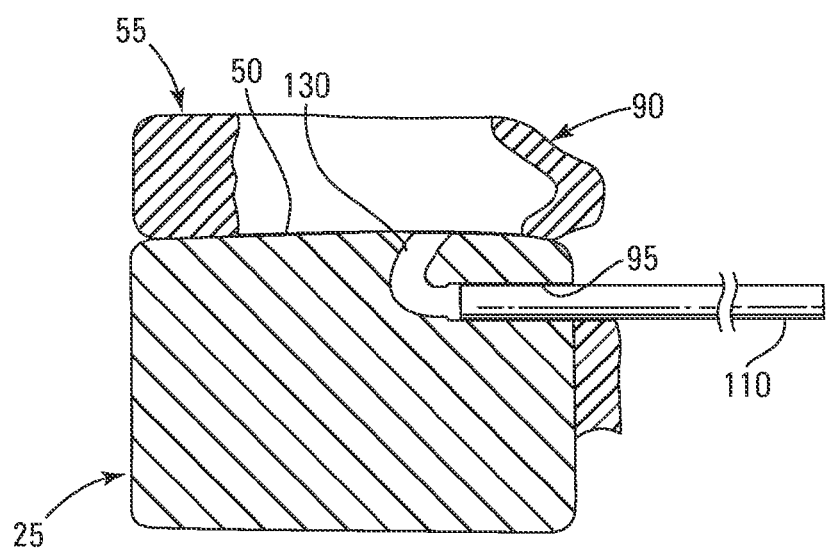

FIG. 3D illustrates the vertebral body 25 after removal of the second boring tool 115. As shown in FIG. 3D, the first and second bore segments 95, 130 are contiguous so as to form the bore 78 extending from the posterior surface 35 through the end plate 50. As further shown, the curved shape of the second bore segment 130 is configured such that an extension of the bore 78 points generally toward the bulged region 90 of the annulus fibrosus 55.

In various embodiments, the flexible distal end portion 122 of the boring tool 115 is formed of a highly flexible, resilient material such that it assumes a generally straight shape when positioned and advanced within the cannula 110, but which tends to assume its pre-formed curved shape when extended distally beyond the cannula 110. In one embodiment, the distal end portion 122 is configured to have sufficient axial stiffness so as not to buckle when pushed through the vertebral body 25. In one embodiment, the distal end portion 122 can be made of a superelastic material such as a superelastic nickel-titanium alloy, e.g., nitinol. In one embodiment, the distal end portion 122 can be made of spring steel. In various embodiments, the proximal portion 120 can be made of the same or different materials having suitable axial and torsional stiffness.

The shape of the pre-shaped bend in the distal end portion 122 of the boring tool 115 is configured to provide the desired shape of the second bore segment 130. In the illustrated embodiment, the distal end portion 122 has a pre-shaped bend extending over an arc of between 90 degrees and 180 degrees such that when extending through the end plate 50, the tip of the distal end portion 122 will be directed toward the bulged region 90 in the annulus fibrosus 55. In other embodiments, other configurations of the distal end portion 122 can be utilized depending on the clinical needs of the patient.

Figure 3E:
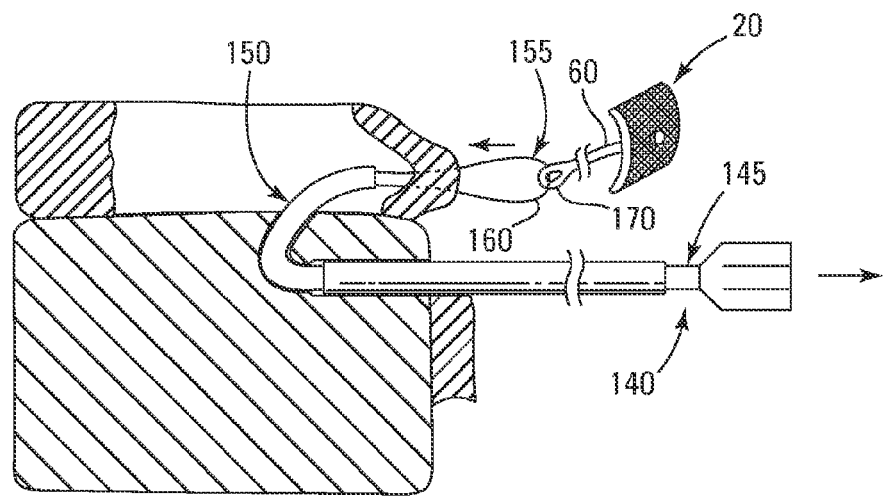

Next, as shown in FIG. 3E, a suture picker 140 is deployed through the cannula 110 to engage the suture element 60 of the repair device 20. As illustrated, the suture picker 140 picker includes a proximal portion 145 and a flexible preshaped distal portion 150 including a distal end 155. As further shown, the distal end 155 is configured to include an engagement feature 160 for engaging the suture element 60. Additionally, the pre-shaped distal portion 150 is configured to direct the distal end 155 toward the annulus fibrosus 55 when the proximal portion 145 is at least partially disposed within the cannula 110 and consequently, the bore 78 (e.g., if the cannula 110 is removed prior to deployment of the suture picker 140).

As illustrated in FIG. 3E, the suture picker 140 extends through the cannula 110 and the second bore segment 130. Additionally, the distal end 155 including the engagement feature 160 extend through the annulus fibrous 55 such that the engagement feature 160 is located external to the annulus fibrosus 55. In the illustrated embodiment, the distal end 155 extends through the bulged region 90, although in various other implementations it can be extended through the annulus fibrosus 55 near, but not necessarily within, the bulged region 90. In various embodiments, the distal end 155 can be routed through an existing opening (e.g., a natural aperture or tear, or a discectomy incision) in the annulus fibrosus 55. In other embodiments, the distal end 155 is configured such that it can pierce the annulus fibrosus 55 without requiring an existing opening or aperture.

As further shown in FIG. 3E, the engagement feature 160 is coupled to the suture element 60 such that the suture element 60 can subsequently be pulled through the annulus fibrosus 55, the bore 78 and cannula 110 and thereafter manipulated by the clinician. In the illustrated embodiment, the engagement feature 160 is a loop formed in the distal end 155 to which a suture loop 170 in the suture element 60 is connected. However, any means for quickly and securely coupling the distal end 155 of the suture picker 140 to the suture element 60 can be utilized within the scope of the invention. Non-limiting examples include one or more hooks formed in the distal end 155 that can engage a portion of the suture element 60, which may include a mating hook comparable feature.

In various embodiments, the distal portion 150 of the suture picker 140, including the distal end 155, are made from a highly flexible and resilient material such as those utilized for the distal end portion 122 of the second boring tool 115. In various embodiments, the proximal portion 145 may be made from the same or different materials.

Figure 3F:
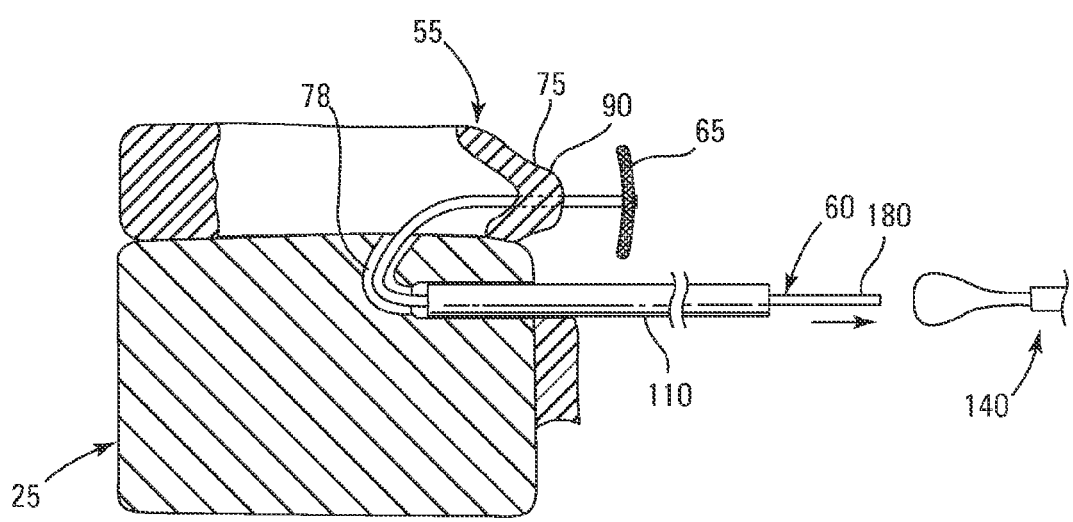
Figure 3G:
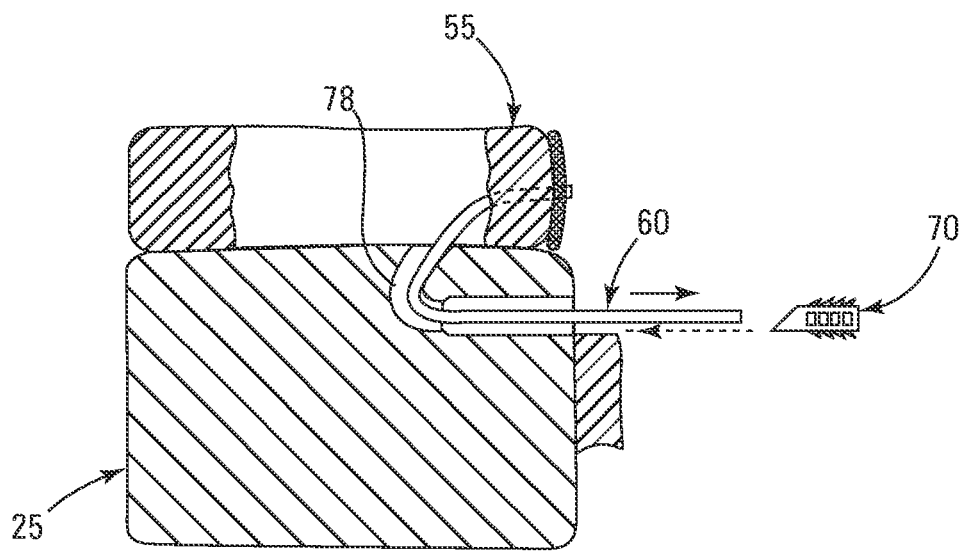

As shown in FIGS. 3F and 3G, with the suture picker 140 fully retracted from the cannula 110, the suture element 60 is then disengaged from the suture picker 140 with a proximal end 180 of the suture element 60 exposed external to the vertebral body 25. If not previously done, the cannula 110 can be removed from the bore 78, and the proximal end 180 of the suture element 60 is pulled proximally so as to draw the patch element 65 against the external surface 75 of the bulged region 90 of the annulus fibrosus 55. Further application of tension on the suture element 60 operates to urge the bulged region 90 anteriorly so as to wholly or substantially reshape the bulged region 90 to approximate the natural shape of the annulus fibrosus 55 (i.e., and consequently, to wholly or substantially eliminate the bulge therein).

Next, as shown in FIG. 3G, the bone anchor 70 is deployed to secure the suture element 60 to the vertebral body 25 under tension so as to retain the annulus fibrosus 55 in its remodeled shape. In the illustrated embodiment, the bone anchor 70 is inserted into the bore 78 and secured therein. As explained above, in one embodiment, the bone anchor 70 is sized to wedge a portion of the suture element 60 between the bone anchor 70 and the inner surface of the bore 78. In one embodiment, the bone anchor 70 is secured within the bore 78 via an interference fit. In the illustrated embodiment, the bone anchor 70 also includes the engagement features (e.g., barbs or projections) that further enhance engagement between the bone anchor 70 and the vertebral body 25 and inhibit expulsion of the bone anchor 70 from the bore 78. In one embodiment, an additional locking element (e.g., a knot, pledget, crimp tube, or the like) can be employed to secure the suture element 60 to the bone anchor 70.

The bone anchor 70 can be deployed using any suitable means. In one embodiment, the bone anchor 70 is deployed into the bore 78 using the fixation delivery apparatus 2010 illustrated in FIGS. 74 and 75A-75B and described in the corresponding detailed description of co-pending and commonly assigned U.S. patent application Ser. No. 12/552,583 filed Sep. 3, 2009, which is incorporated herein by reference in its entirety. In such embodiments, the bone anchor 70 is releasably coupled within the tubular shaft of the fixation delivery apparatus, the distal end of which is inserted into the bore 78. The bone anchor is thereafter ejected from the tubular shaft of the fixation delivery apparatus (e.g., via an ejection rod disposed within the tubular shaft), and caused or allowed to positively engage the inner surface of the bore to secure the bone anchor 70 and consequently, the suture element 60, to the vertebral body 25.

Figure 4:
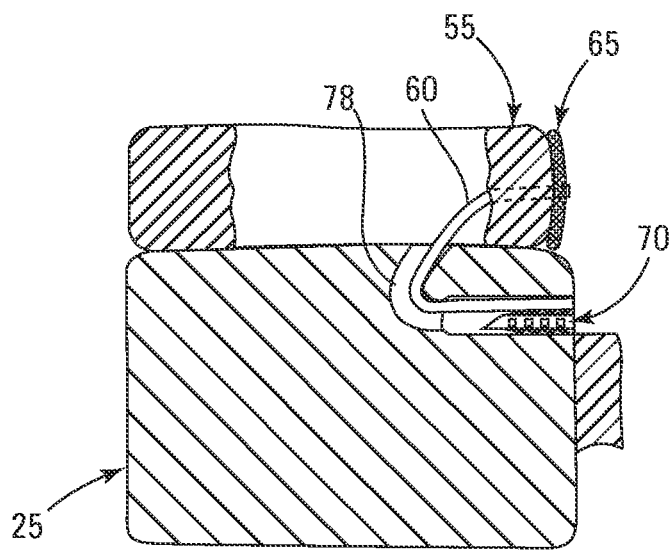
FIG. 4 is a partial cross-sectional elevation view illustrating an annulus fibrosus of an intervertebral disc repaired using the repair device of FIGS. 1A-1B and 2.

Once the bone anchor 70 is securely deployed to attach the suture assembly to the vertebral body 25, any excess length of the suture assembly 60 can be cut away and removed. FIG. 4 illustrates the repaired an annulus fibrosus 55 with the repair device 20 fully implanted according to one embodiment.

In the embodiments described herein, the bone anchor 70 is deployed into the bore 78. In other embodiments the suture element 60 can be secured to the vertebral body 25 using one or more bone anchoring means in addition to or in lieu of the bone anchor 70 positioned in the bore 78. Exemplary such bone anchoring means include, without limitation, staples, screws, bone cement, and the like.

In addition, while in the illustrated embodiments the bore 78 is formed through the superior end plate 50, the invention is not so limited. For example, in other embodiments, depending on the clinical needs of the patient, the bore 78 can be formed through the inferior end plate 52 (i.e., the vertebral body 25 lies superiorly to the intervertebral disc being repaired).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of reducing a bulge in an intervertebral disc annulus fibrosus adjacent to a vertebral body of a patient's spine, the vertebral body having a posterior surface and an end plate adjacent to the annulus fibrosus, the method comprising:
   forming a bore through a portion of the vertebral body, the bore extending from the posterior surface and through the end plate;
   advancing a suture picker through the bore and into the intervertebral disc;
   advancing a distal end of the suture picker through an outer surface of the annulus fibrosus at a location within or proximate the bulge;
   engaging the distal end of the suture picker with a portion of a flexible suture element connected to a flexible patch element;
   retracting the distal end of the suture picker and the portion the suture element engaged therewith proximally through the annulus fibrosus and the bore in the vertebral body, such that the portion of the suture element is positioned external to the vertebral body;
   applying tension to the portion of the suture element so as to draw the patch element against the outer surface of annulus fibrosus at the location within or proximate the bulge and urge the annulus fibrosus within or proximate the bulge toward an anterior portion of the annulus fibrosus; and
   securing the suture element under tension.

2. The method of claim 1 wherein applying tension to the portion of the suture element substantially reshapes the annulus fibrosus to substantially its natural shape.

3. The method of claim 1 wherein forming the bore includes forming a first bore segment with a first boring tool, and subsequently forming a second bore segment distal to the first bore segment using a second boring tool.

4. The method of claim 3 wherein the first bore segment extends generally parallel to the end plate, and wherein the second bore segment extends distally from the first bore segment along a curved path toward and through the end plate.

5. The method of claim 4 wherein the first boring tool is a bone awl having a generally straight working shaft, and wherein the second boring tool includes a flexible distal end portion pre-shaped so as to define the curved path.

6. The method of claim 5 wherein forming the bore further includes inserting a generally rigid tubular cannula into the first bore segment prior to forming the second bore segment.

7. The method of claim 6 wherein forming the second bore segment includes advancing the second boring tool through the tubular cannula, the tubular cannula maintaining the flexible distal end portion of the second boring tool in a deflected, substantially straight configuration.

8. The method of claim 7 wherein the flexible distal end portion of the second boring tool is configured to assume its pre-shaped configuration once extended beyond the tubular cannula so as to form the second bore segment upon advancement through the vertebral body distal to the tubular cannula.

9. The method of claim 1 wherein the suture picker includes a proximal portion and a flexible, pre-shaped distal portion including the distal end, the pre-shaped distal portion configured to direct the distal end toward the annulus fibrosus when the proximal portion is at least partially disposed within the bore.

10. The method of claim 9 wherein the distal end includes an engagement feature for engaging the suture element.

11. The method of claim 10 wherein the suture element includes a suture loop for engaging the engagement feature of the suture picker.

12. The method of claim 1 wherein advancing the distal end of the suture picker through the outer surface of the annulus fibrosus includes advancing the distal end through an opening in the annulus fibrosus within the bulge.

13. The method of claim 12 wherein the opening is an incision made by a clinician during a discectomy procedure.

14. The method of claim 1 wherein securing the suture element under tension includes securing the suture element to the vertebral body.

15. The method of claim 14 wherein securing the suture element to the vertebral body includes deploying a bone anchor into the bore and securing the bone anchor to the suture element and to the vertebral body within the bore with the suture element maintained in tension.

16. The method of claim 15 wherein the bone anchor is configured to receive the suture element, and wherein attaching the bone anchor to the suture element includes positioning an end of the suture element within the bone anchor and advancing the bone anchor along the suture element.

17. The method of claim 16 wherein advancing the bone anchor along the suture element includes advancing the bone anchor along the suture element and into the bore in the vertebral body, and wherein attaching the bone anchor to the vertebral body includes attaching the bone anchor to the vertebral body within the bore.

18. The method of claim 15 wherein securing the suture element to the vertebral body includes securing a portion of the suture element between the bone anchor and the inner surface of the bore.

19. The method of claim 18 wherein securing the bone anchor to the vertebral body within the bore includes forming an interference fit between the bone anchor and an inner surface of the bore.

20. The method of claim 15 wherein the bone anchor includes a bone engagement feature, and wherein attaching the bone anchor to the vertebral body includes engaging the vertebral body with the bone engagement feature.

21. The method of claim 20 wherein the bone engagement feature includes one or more barbs or projections configured to allow the bone anchor to be advanced distally within the bore and to inhibit subsequent proximal movement of the bone anchor within the bore toward the posterior surface of the vertebral body.

22. The method of claim 15 wherein attaching the bone anchor to the suture element includes securing the suture element to the bone anchor to prevent relative movement of the bone anchor and the suture element after attaching the bone anchor to the vertebral body.

* * * * *